United States Patent
Burger

[11] 3,966,602
[45] June 29, 1976

[54] PROCESS AND APPARATUS FOR RECLAIMING AND REGENERATING SPENT SOLVENT

[75] Inventor: Charles Frederic Burger, Geneva, Switzerland

[73] Assignee: E. I. Du Pont de Nemours and Company, Wilmington, Del.

[22] Filed: Aug. 29, 1974

[21] Appl. No.: 501,790

[30] Foreign Application Priority Data
Sept. 17, 1973 Switzerland.................... 13300/73

[52] U.S. Cl................................ 210/83; 68/18 R; 137/119; 137/172; 210/96 R; 210/101; 210/105; 210/127; 210/139; 210/197
[51] Int. Cl.² ................... B01D 17/02; B01D 21/10
[58] Field of Search................ 8/142, 158; 68/18 R; 210/83, 96, 101, 104, 105, 114, 127, 138, 139, 140, 167, 197, 207, 515; 137/119, 172

[56] References Cited
UNITED STATES PATENTS

| | | | |
|---|---|---|---|
| 1,691,060 | 11/1928 | Harrison ............................. | 210/83 |
| 2,913,893 | 11/1959 | Mathews et al....................... | 8/142 |
| 2,940,287 | 6/1960 | Henderson ..................... | 68/18 R X |
| 3,206,951 | 9/1965 | Sieber ........................... | 68/18 R X |
| 3,253,711 | 5/1966 | Young .......................... | 137/119 X |
| 3,269,155 | 8/1966 | Shaw............................... | 210/114 X |
| 3,273,576 | 9/1966 | Fluegel et al. ..................... | 210/96 X |
| 3,561,917 | 2/1971 | Michaels et al........................ | 8/142 |
| 3,728,074 | 4/1973 | Victor............................. | 68/18 R X |

FOREIGN PATENTS OR APPLICATIONS

| | | | |
|---|---|---|---|
| 1,165,766 | 10/1958 | France............................... | 137/172 |
| 1,258,747 | 12/1971 | United Kingdom................... | 210/96 |

*Primary Examiner*—Charles N. Hart
*Assistant Examiner*—Robert G. Mukai

[57] ABSTRACT

The invention is directed to process and apparatus for automatically restoring to usefulness spent cleaning and/or drying liquids comprising an aqueous phase and an oil phase, the latter comprising 1,1,2-trichloro-1,2,2-trifluoroethane, as the principal component, and a surfactant, said process and apparatus characterized in that electrical conductometric means, liquid level sensing means and time programmed means cooperate and automatically direct separation and removal means in the separation and removal of the aqueous phase from the oil phase, said process further characterized in that, optionally, at least one of the group consisting of 1,1,2-trichloro-1,2,2-trifluoroethane, surfactant and water is added to the oil phase, the amount of water added being insufficient to produce an aqueous phase, to restore the oil phase to usefulness as a cleaning and/or drying liquid.

5 Claims, 5 Drawing Figures

PROCESS AND APPARATUS FOR RECLAIMING AND REGENERATING SPENT SOLVENT

BACKGROUND OF THE INVENTION

1. Field of the Invention

This invention relates to cleaning and/or drying liquids, and more specifically, to process and apparatus for separating and removing the aqueous phase from the oil phase of spent cleaning and/or drying liquids.

2. Description of the Prior Art

Solutions of surfactants in liquid chlorocarbons and chlorofluorocarbons capable of solubilizing water have found important industrial uses. Employed as cleaning liquids, such solutions containing solubilized water are frequently capable of dissolving not only those soils which are soluble in the chlorocarbon or chlorofluorocarbon but also those which are usually soluble only in water. Frequently, such solutions are also capable of emulsifying insoluble soils. The unusual properties of these liquids have led to their extensive use in cleaning, such as in the cleaning of industrial articles, and in the drycleaning of textile materials. Liquids of this kind and which are not saturated with respect to solubilized water have also been employed for the drying of water-wet articles in processes wherein the water adhering to the articles is solubilized by the liquid mixture.

Solutions comprising a chlorofluorocarbon, particularly 1,1,2-trichloro-1,2,2-trifluoroethane, are known in the art for the cleaning and/or drying of sensitive materials, such as plastic electronic assemblies. Swiss Patent 445,001 includes a disclosure of such a solution. Chlorocarbons, because of their greater aggressiveness, are often not suitable for such a use. Of the liquids described in the Swiss patent, the combination of 1,1,2-trichloro-1,2,2-trifluoroethane, about 2 weight % of isopropylammonium dodecylbenzenesulfonate as surfactant and about 6 weight % of solubilized water has been employed in the trade, particularly for the cleaning of, and sometimes for the drying of, precision metal parts and plastic articles. The patent further discloses that small amounts of aqueous ammonia can be added for special cleaning purposes and that specified inhibitors can be added to prevent reaction of the composition with reactive metals. Such liquids comprising a chlorocarbon or chlorofluorocarbon, a surfactant and solubilized water may be unstable toward electrolytes. Hence, in uses wherein such a liquid imbibes electrolytes from the articles being cleaned or dried, the liquid becomes spent. As the term is used herein, a spent liquid or solution is one wherein some of the solubilized water has separated from the oil phase to form an aqueous phase. The Swiss patent discloses that, to restore the spent cleaning and/or drying liquid to usefulness, the aqueous phase, which contains most of the electrolytes, should be separated (from the oil phase) and discarded and, optionally, fresh water should thereafter be added to the oil phase and, optionally, to overcome operational losses, an appropriate amount of 1,1,2-trichloro-1,2,2-trifluoroethane should be added. In overcoming operational losses, the make-up liquid usually employed consists of 1,1,2-trichloro-1,2,2-trifluoroethane and a surfactant which is dissolved therein at a concentration equal to about one-third to one-half of the surfactant concentration in the original drying and/or cleaning liquid. In connection with the optional addition of fresh water, publicly available water supplies are generally of sufficient purity for the regeneration of spent liquids. For drying liquids, it is to be understood that water should not be added to the oil phase.

The above-described restoration process for spent liquids does not remove soils dissolved in the oil phase. However, since the appearance of an aqueous phase generally occurs much before the liquid is overloaded with chlorofluorocarbon soluble soils, regeneration of the oil phase, as described above, substantially extends the useful life of the liquid. In other words, the liquid can be regenerated one or more times before there is objectionable buildup of soil.

Cleaning and/or drying liquids other than those described above but comprising a chlorofluorocarbon and an alkylbenzenesulfonate surfactant also are known in the art. For example, amine-neutralized undecyl- and tridecyl-benzene-sulfonic acids are surfactants for the solubilization of water in trichlorofluoromethane, 1,1,2,2-tetrachloro-1,2-difluoroethane or 1,1,2-trichloro-1,2,2-trifluoroethane. Such compositions are useful as cleaning and/or drying liquids. It is also known that non-ionic surfactants can be advantageously added to the aforesaid undecyl- and tridecyl-benzene-sulfonate chlorofluorocarbon compositions and mixed amine salts of dodecylbenzenesulfonic acid are known to be suitable as surfactants in trichlorotrifluoroethane. Such compositions also are useful as cleaning and/or drying liquids.

Surfactants other than alkylbenzenesulfonates are also known to be useful for the solubilization of water in chlorofluorocarbons and, thus, for the formulation of cleaning and/or drying liquids. For example, solutions of alkali metal salts of dioctyl sulfosuccinate in 1,1,2-trichloro-1,2,2-trifluoroethane and the corresponding amine salts in chloro- and bromo-hydrocarbon solvents exhibit such utility.

Of the above-described liquids or solutions, those which are most useful as cleaning and/or drying liquids are those wherein the surfactant tends to remain in the oil phase, thus minimizing loss of surfactant in the aqueous phase which is discarded. The alkylbenzenesulfonates exhibit this property and, for this reason, generally are preferred. Trade use of the above-described liquids has been hindered by difficulties which are inherent in known methods for regenerating spent liquids.

SUMMARY OF THE INVENTION

It is an object of this invention to provide process and apparatus for the automatic restoration of spent cleaning and/or drying liquids.

This invention provides process and apparatus for automatically restoring to usefulness spent cleaning and/or drying liquids containing, when spent, an aqueous phase and an oil phase, the latter comprising 1,1,2-trichloro-1,2,2-trifluoroethane, as principal component, and a surfactant, said process comprising the steps:

1. collecting and storing spent solvent for a period of time sufficient to permit the spent solvent to separate into an upper aqueous phase and a lower oil phase;
2. discharging the separated, stored spent solvent by sequentially discharging the oil phase and the aqueous phase through an automatic liquid phase detector and transmitter to detect and transmit a signal indicating the presence of the oil phase and the presence of the aqueous phase as they sequentially pass through the liquid phase detector and transmitter; and 3. receiving the signal transmitted by the automatic liquid phase detector and transmitter by valve means that sequentially receives the signal indicating the presence of the oil phase and directs the oil phase through conduit means to an oil phase reservoir and receives the signal indicating the presence of the aqueous phase and directs the aqueous phase through conduit means to waste.

Said apparatus comprises:

1. a first vessel to hold spent solvent for a period of time sufficient to permit the spent solvent to separate into an upper aqueous phase and a lower oil phase, said first vessel having a liquid entry port to receive spent solvent and a liquid discharge port to discharge the liquid contents of the vessel;
2. an automatic liquid phase detector and transmitter connected in liquid relationship with the liquid discharge from the first vessel to detect and transmit a signal indicating the presence of the oil phase and the presence of the aqueous phase as they sequentially pass through the liquid phase detector and transmitter;
3. a second vessel to hold the oil phase and having a liquid entry port to receive the oil phase; and
4. valve and conduit means to conduct liquid from the liquid discharge port of the first vessel through the automatic liquid phase detector which sequentially detects the presence of the oil phase and transmits a signal to the valve means to direct the flow of oil phase into the liquid entry port of the second vessel and detects the presence of the aqueous phase and transmits a signal to the valve means to direct the flow of aqueous phase to waste.

DETAILED DESCRIPTION OF THE INVENTION

Figure 1:
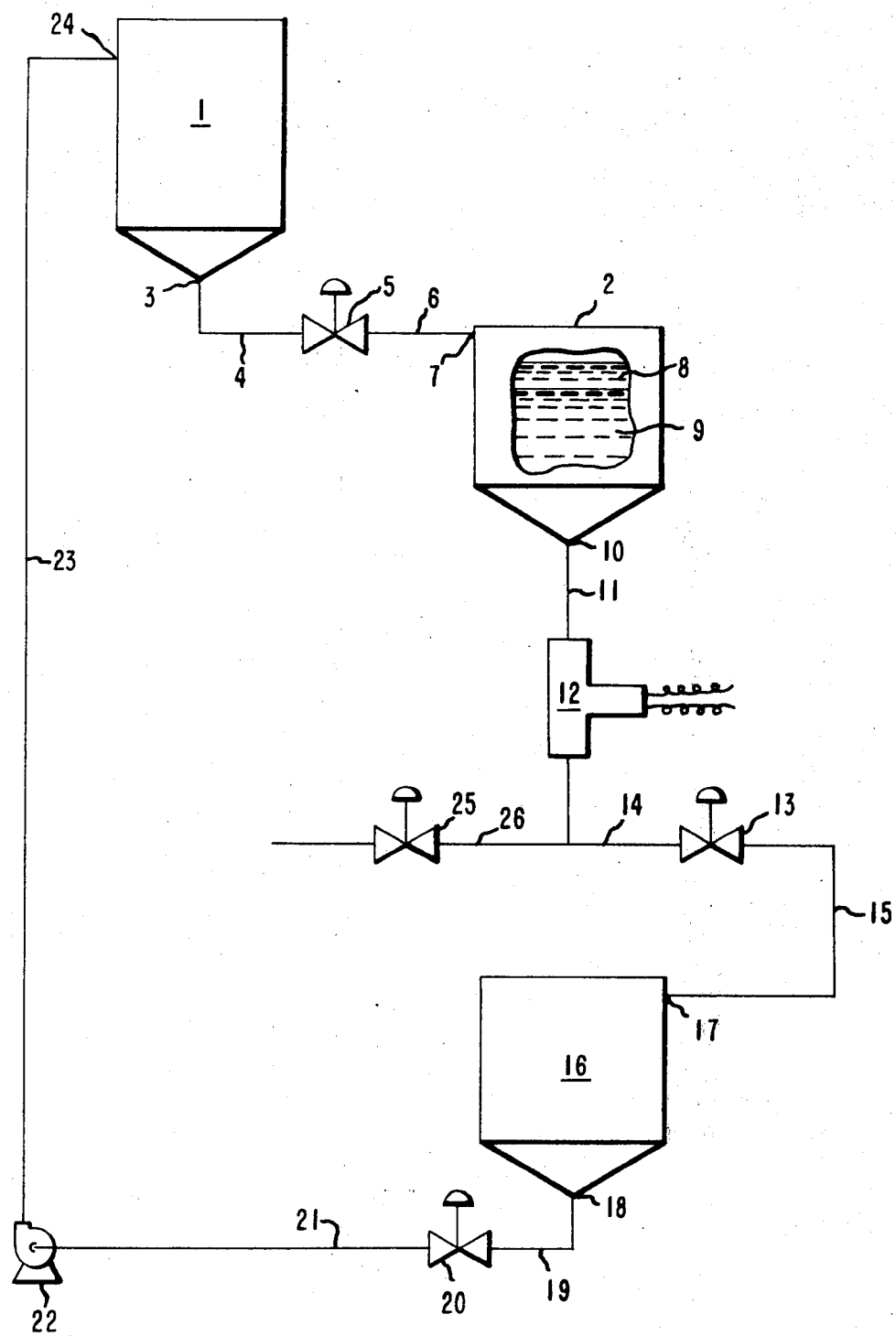
FIGS. 1 and 5 are flow sheets showing embodiments (with a single decanter) for carrying out the process of the invention.

The process and apparatus of this invention are defined above in the Summary. The present invention is useful both in cleaning operations, wherein the initial charge of the cleaning solution is made up of a major portion of an oil phase and a minor portion of an aqueous phase, and in drying operations, wherein the initial charge is made up of an oil phase. The initial charge is hereinafter referred to as the solvent. Regeneration is dependent on the operation being performed. With cleaning solutions, regeneration is accomplished by adding to the reclaimed solvent the same amount of water that is discharged to waste and an amount of oil which is sufficient to replace operational losses. As already indicated, when the solvent is being used in a drying operation, it is made up only of an oil phase. However, during the drying operation, the oil phase picks up water which is separated and removed from the spent solvent as disclosed above. Thereafter, regeneration is accomplished by adding only fresh oil phase components to the reclaimed solvent to replace operational losses. Various embodiments of this invention will now be described in conjunction with the drawings. The basic apparatus and process for reclaiming spent solvent is depicted in FIG. 1. Solvent being used as a cleaning or drying agent is contained in work bath vessel 1. After the solvent in vessel 1 is spent, it is transferred from exit port 3 through conduit 4, automatic valve 5, conduit 6 and fluid entry port 7 into collecting and holding vessel 2. The spent solvent is held in vessel 2 for a period of time sufficient to permit the spent solvent to separate into an upper aqueous phase 8 and a lower oil phase 9. After separation, liquid is drawn from the bottom of holding vessel 2 through exit port 10 and conduit 11 into an automatic liquid phase detector and transmitter 12 to detect and transmit a signal indicating first the presence of the oil phase and thereafter the presence of the aqueous phase as the phases pass sequentially through the liquid phase detector and transmitter. The signal transmitted by detector and transmitter 12 indicating the presence of the oil phase is received by automatic valve 13; the signal actuates and opens valve 13. When valve 13 opens, the oil phase passes through conduit 14, valve 13 and conduit 15 into the oil phase storage vessel 16 through fluid entry port 17. The reclaimed oil phase is stored in vessel 16 until it is needed as a working solvent again. Then it is fed back into the main operating system through fluid exit port 18, conduit 19, valve 20, conduit 21, pump 22, conduit 23 and fluid entry port 24 into working bath vessel 1. The signal transmitted by detector and transmitter 12 indicating the presence of the aqueous phase is received by automatic valve 25; the signal actuates and opens valve 25. Simultaneously, the signal that indicated the presence of the oil phase terminates and valve 13 closes; the flow of the aqueous phase thus is directed through conduit 26 and open valve 25 to waste. When the flow of aqueous phase to waste is completed, the signal transmitted by detector and transmitter 12 to valve 25 terminates, causing valve 25 to close.

All of the vessels, piping and valves and the detector-transmitter are commercially available. Critical to the operation is the detector-transmitter which sequentially detects and transmits the signals indicating the presence of the oil phase and the aqueous phase and which has the capability of detecting the interface between the oil phase and the aqueous phase in a flowing stream of spent solvent. The interface detection is provided by an in-line electrical conductometric probe having two electrodes exposed to the stream. When aqueous phase is between the electrodes, sufficient current flows between the electrodes under an impressed voltage to generate, by a resistance-sensing amplifier, an electrical output signal. When oil phase or air is between the electrodes, insufficient current flows between the electrodes to cause the generation of an output electrical signal. The presence or absence of an electrical signal is used to activate and deactivate solenoid valves to appropriately direct the flow of the oil phase and the aqueous phase.

Figure 2:
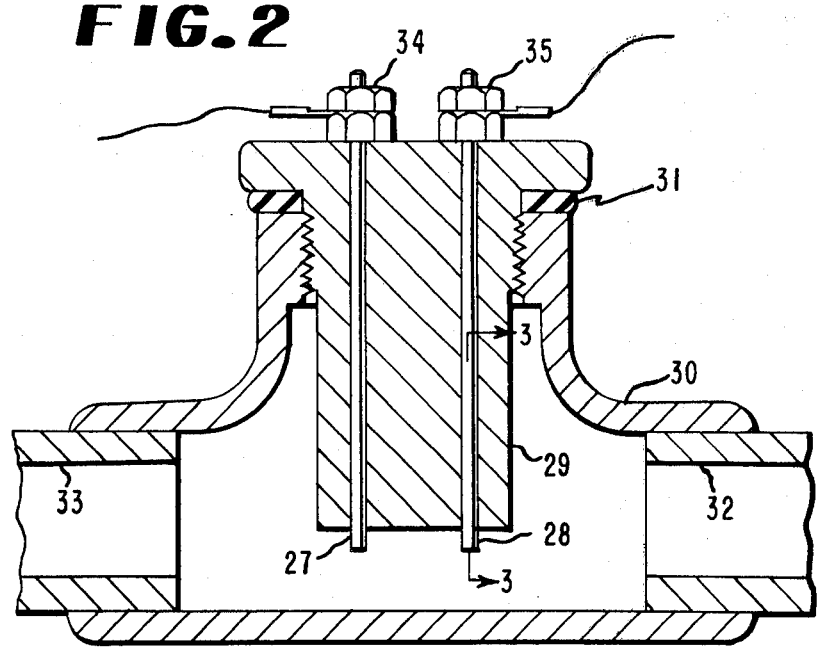
FIG. 2 is a longitudinal sectional view of one embodiment of an in-line electrical conductometric probe for detecting the presence of an aqueous phase in a flowing stream of spent cleaning liquid.
Figure 3:
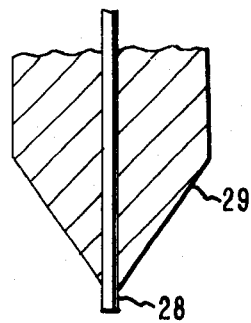
FIG. 3 is a sectional view showing the tip of the electrode-supporting body of FIG. 2 taken along the plane 3—3.

FIGS. 2 and 3 depict a preferred embodiment of an in-line liquid phase detector and transmitter with electrical conductometric interface detection means. In FIG. 2, electrodes 27 and 28, preferably of conductive corrosion resistant metal, such as a stainless steel, are sealed in a liquid tight manner in electrode holder 29, fabricated from electrically non-conductive material, preferably unplasticized polyvinyl chloride. Electrode holder 29 is fixed in tee 30, preferably by means of matching threads so as to form a liquid tight seal between electrode holder 29 and tee 30 by means of gasket 31. The inner end of electrode holder 30 is preferably tapered in two planes so as to support electrodes 27 and 28 without excessively restricting the flow of spent liquid through tee 30. Pipes 32 and 33 are welded to tee 30 and connect the detector-transmitter in fluid relationship with the flow of spent solvent. Electrical connectors 34 and 35 communicate with the resistance sensing amplifier (not shown). When, as is preferred, a voltage of 220 volts A.C. (alternating current) is impressed across electrodes 27 and 28 and 0.1 MA (milliampere) is the threshold current for generation of an electrical ouput signal by the resistance-sensing amplifier, it is preferred to employ electrodes 27 and 28 of cylindrical shape, about 2 mm. in diameter, and to place them in electrode holder 29 so that they extend outwardly from electrode holder 29 about 1 mm. and so that they are about 9 mm. apart, center to center. FIG. 3 shows the inner end of electrode holder 29 in a plane taken at right angles to the view of FIG. 2, that us, along the line 3—3 of FIG. 2. FIG. 3 shows a preferred manner of tapering the inner end of electrode holder 29. Other detector-transmitters with means adaptable to the detection of a liquid phase interface are commercially available. Such adaptable means include gravimetric, refractive and spectrophotometric means which, however, are less preferred than the electrical conductometric means described alone.

Only the functional parts of the embodiments as they pertain to the invention are described herein. The selection of other parts which, although they may be necessary to the general operation of the process and apparatus of this invention, are not actually part of the invention is within the skill of any artisan in the field of cleaning and/or drying liquids and their use. For example, should the operation involve buildup of troublesome amounts of insoluble debris in the work bath, it may be useful to provide for filtering the spent liquid before passing it to the restoration unit. Also, it may be useful to provide for flushing the work bath vessel with liquid from the restoration unit (to remove sediment) before returning restored liquid to it. Still further, the pump referred to above may also be employed in the filtration of the liquid in the work bath during the operation of the process.

In regenerating reclaimed solvent by adding water and/or oil (which optionally contains surfactant), the amounts added can be controlled by calibrating the liquid holding vessel with level sensing means which operate to provide for the closing of a solenoid valve controlling the addition when the liquid level reaches a predetermined level. A preferred level sensing means comprises a float capable of actuating an electrical switch when the float, responding to the liquid level, reaches a predetermined height. The most preferred means comprises a known float type limit switch wherein a magnet-containing float slidingly surrounds a non-magnetic vertical tube containing, at a predetermined level, a magnetically actuated reed type switch. In those embodiments of the invention wherein the amounts of the additions are controlled by level sensing means, such as that depicted in FIG. 4, the amounts are predetermined by volume. The preferred volumes are those which return the cleaning and/or drying liquid approximately to its original condition. Although it may be advantageous to adjust level sensing floats (which measure effective specific gravity) so as to sense the level of the interface, it is preferred to adjust the float so that it senses the level of the aqueous phase, if present, or the level of the oil phase.

Figure 5:
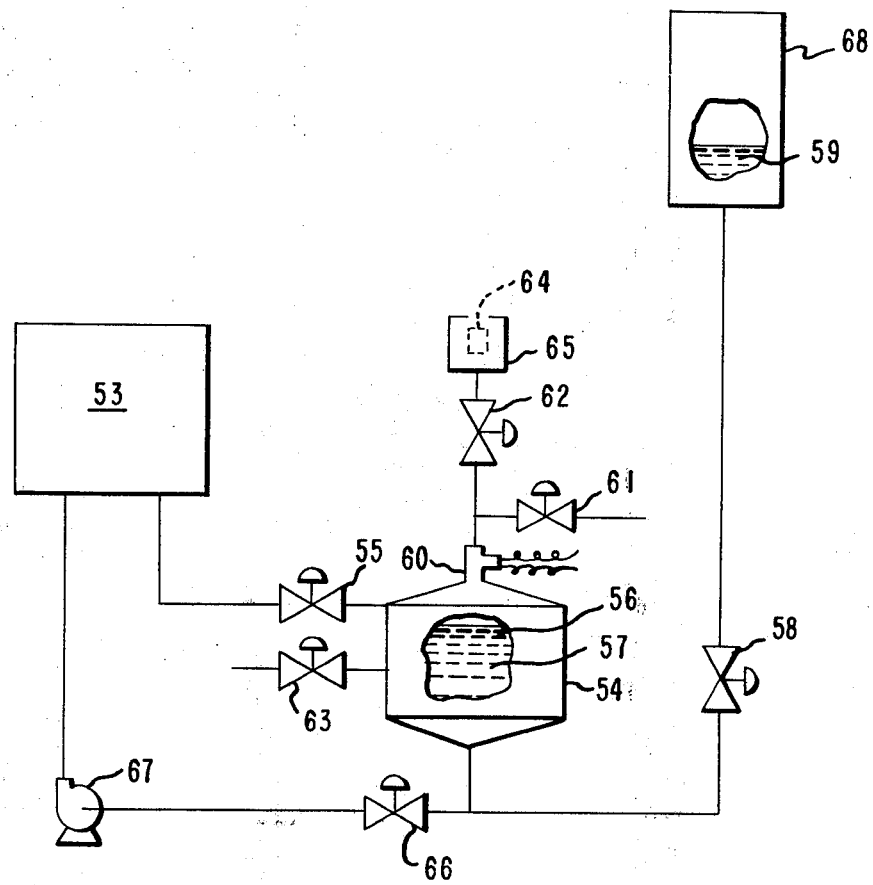

In some embodiments, the volumes of the additions are not predetermined by level sensing means. As shown in the embodiment of FIG. 5 (described hereinafter), for example, the volume of water added to the liquid holding vessel is fixed by means of an electrical conductometric probe and associated resistance sensing amplifier at a value equal to the volume of the aqueous layer discarded. The liquid holding vessel in this embodiment is still considered to be a calibrated vessel. Also useful in the automatic processes of the invention is a programmed timer, hereinafter called a programmer. In brief, the programmer is a device for providing electrical impulses at programmed times and for predetermined periods of time. The programmer, therefore, provides time dependent control of the process. It can, for example, suspend the process for a time sufficient to permit the spent cleaning and/or drying liquid to separate into an aqueous phase and an oil phase and, after separation is complete, direct the continuation of the process. Similarly, the programmer, by means of appropriate relays, may control other process steps which operate at predetermined times. Alternatively, the programmer may, at appropriate times, use the level sensing means and the interface sensing means to control the process and permit cooperating means, such as solenoid valves, to function in response to the directives of such sensing means. This is easily done by causing the programmer to select a circuit wherein the level and/or interface sensing means are in series relationship between the programmer and one or more solenoid valves. Similarly, the programmer, at appropriate times, may remove control of the process from the sensing means. Various types of readily available programmers can be employed. It is preferred to employ a device, not shown in the drawings, wherein a perforated program card is driven by means of an electric clock motor over the actuating knobs of a series of limit switches arranged normally in a line perpendicular to the direction of travel of the card. The actuating knobs are spring loaded so as to cause them to bear against the card. When a perforation, positioned according to the needs of the process, comes into register with an actuating knob, the knob moves outwardly into the perforation, thus closing or opening the circuit of which the switch is a part. The longitudinal position and length of the perforations are selected according to the speed with which the card is driven and the needs of the process. Such programmers are readily available in the trade.

Figure 4:
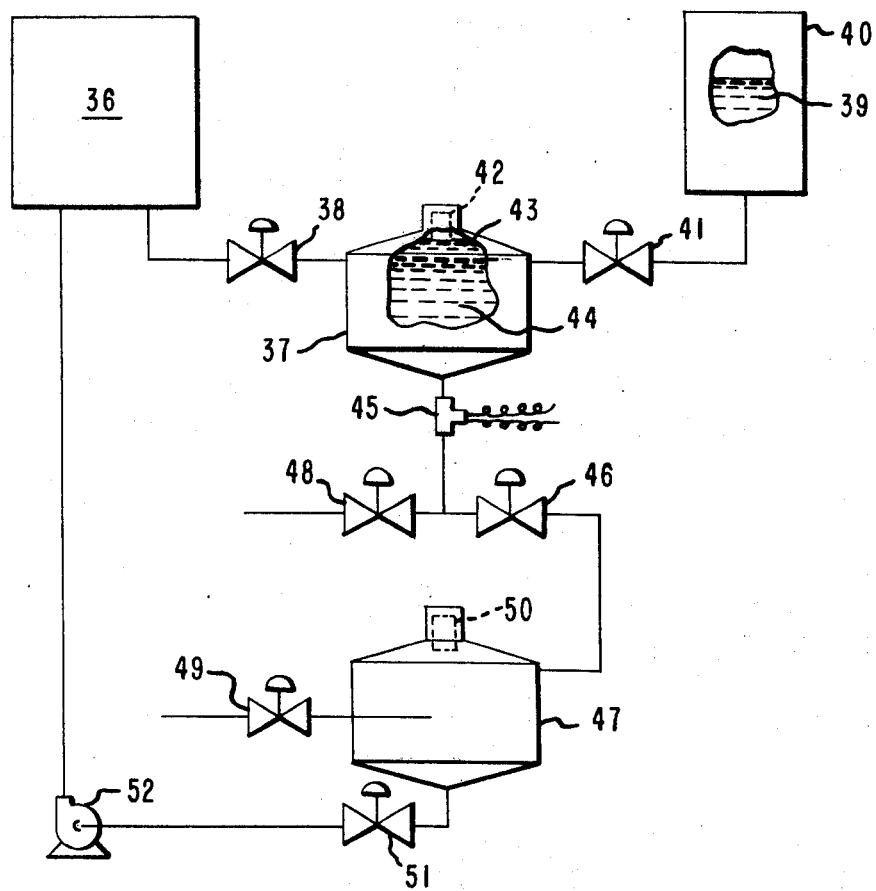
FIG. 4 is a flow sheet of a preferred device (with two decanters) for carrying out the process of the invention.

FIG. 4 shows a solvent cleaning system wherein the spent solvent is reclaimed and regenerated by the addition of clean water and oil in an amount sufficient to make up for operational losses. In the embodiment of FIG. 4, spent cleaning solvent in work bath 36, wherein articles to be cleaned are contacted, is transferred into decanter 37 upon either the programmed or manual opening of solenoid valve 38. Following a programmed time interval sufficient for the above transfer to occur, upon programmed opening of solenoid valve 41 oil 39 is admitted to decanter 37 from reservoir 40. The electrical circuit connecting the programmer and solenoid valve 41 passes in series through float-actuated switch 42. When the liquid level in decanter 37 reaches a predetermined level to which the float of float-actuated switch 42 is raised, the circuit is broken and solenoid valve 41 closes. The contents of decanter 37 are allowed to stand for a programmed period of time sufficient for the aqueous phase 43 to separate from the oil phase 44. FIG. 4 shows the liquid level after separation has been completed. It is frequently convenient to allow the separation to occur during non-working hours. The programmer then energizes electrical conductometric probe 45 and associated resistance sensing amplifier (not shown) and causes solenoid valve 46 to open, permitting oil phase 44 to flow into decanter 47. When the aqueous phase 43, which follows the oil phase 44, reaches the electrodes of electrical conductometric probe 45, an output signal generated by the associated resistance sensing amplifier (not shown) causes solenoid valve 46 to close and solenoid valve 48 to open, permitting the discharge of the aqueous phase 43. Thereafter, the programmer deenergizes electrical conductometric probe 45 and solenoid valves 46 and 48 and, through a circuit in series relationship with float-actuated switch 50, energizes and opens solenoid valve 49. Fresh water is admitted through solenoid valve 49, from a source not shown, to decanter 47 until the liquid level therein reaches a predetermined level, at which time float-actuated switch 50 opens the circuit to solenoid valve 49, causing it to close. The liquid now in decanter 47 is regenerated solvent. Solenoid valve 51 and pump 52 is energized by programmed means or manually, the latter preferred, to return the regenerated solvent of decanter 47 to work bath 36 for further service. Thereafter, all actuation is shut off.

FIG. 5 shows another embodiment wherein the aqueous phase is removed from the top of a decanter. There is advantage in this mode of operation because somewhat sharper separation can be made between the aqueous phase and the oil phase since the electrical conductometric probe of the liquid phase detector and transmitter can be operated more smoothly. In the embodiment of FIG. 5, spent cleaning liquid is transferred from work bath 53 to decanter 54 on manual or programmed opening of solenoid valve 55. The programmer interrupts further processing for a time sufficient for the aqueous phase 56 to separate from the oil phase 57. FIG. 5 shows the liquid levels after separation has been completed. The programmer then energizes solenoid valve 58 to admit oil make-up liquid 59 in reservoir 68 to decanter 54 by an in-series circuit through a relay operated by the resistance sensing amplifier associated with electrical conductometric probe 60 so that, when rising aqueous phase 56 passes through electrical conductometric probe 60, solenoid valve 61 is opened, permitting the discharge of the aqueous phase 56. When aqueous phase 56 is displaced in the electrical conductometric probe 60 by the rising oil phase 57, the associated resistance sensing amplifier (not shown) causes solenoid valves 61 and 58 to close and solenoid valve 62 to open. At the same time, electrical conductometric probe 60 is deenergized and solenoid valve 63, through an electrical circuit in series with floatactuated switch 64, is opened to admit fresh water, from a source not shown, to decanter 54. When the level of oil phase 57 reaches a predetermined level in auxiliary reservoir 65, float-actuated switch 64 opens the circuit between the programmer and solenoid valve 63, causing solenoid valve 63 to close. Solenoid valve 62 remains open. The oil phase 57 is returned to work bath 53 from decanter 54 and auxiliary reservoir 65 by programmed or manual actuation of solenoid valve 66 and pump 67. Thereafter, all actuation is shut off.

In the present invention the terms "oil" and "oil phase" are intended to include liquid chlorocarbons and chlorofluorocarbons that are used alone or mixed with a minor amount of water and/or surfactant and used as a cleaning agent or as a drying agent. Oil, oil-water, oil-surfactant and oil-water-surfactant compositions which are known in the art and which have been previously discussed herein in the prior art section are especially useful in the process and apparatus of this invention.

I claim:

1. Apparatus for reclaiming and regenerating spent solvent which is made up of a major portion of an oil phase and a minor portion of an aqueous phase and which has been used in a cleaning operation, which apparatus comprises:
   1. a first vessel to hold spent solvent for a period of time sufficient to permit the spent solvent to separate into an upper aqueous phase and a lower oil phase, said first vessel having a liquid entry port to receive spent solvent and a liquid discharge port to discharge the liquid contents of the vessel;
   2. an automatic liquid phase detector-transmitter connected in liquid relationship with the liquid discharge from the first vessel to generate an appropriate electrical signal indicating the presence or absence of the aqueous phase or the oil phase as either phase passes through the detector-transmitter, said detector-transmitter comprising an in-line electrical conductometric probe having two electrodes exposed to the liquid discharge stream from the first vessel;
   3. a second vessel to hold the oil phase and having a liquid entry port to receive the oil phase; and
   4. valve and conduit means, said valve means being controlled by a programming means which is actuatable by the electrical signal generated by the detector-transmitter, to conduct liquid from the liquid discharge port of the first vessel through the automatic liquid phase detector-transmitter and to direct the flow of oil phase into the liquid entry port of the second vessel and the flow of aqueous phase to waste, said apparatus further comprising means to regenerate the reclaimed oil phase, said means comprising a vessel containing fresh oil, an automatic valve and conduit means controlled by said programming means to conduct liquid from the fresh oil-containing vessel to the first vessel which is calibrated to hold a predetermined amount of solvent, a water reservoir, an automatic operating valve and conduit means controlled by said programming means to conduct water from the water reservoir through the automatic operating valve and into the second vessel which is calibrated to hold all the oil transferred from the first vessel and the amount of water equivalent to the amount of aqueous phase discharged to waste.

2. Process for reclaiming and regenerating spent solvent which is made up of a major portion of an oil phase and a minor portion of an aqueous phase and which has been used in a cleaning operation, which process comprises the steps:

1. collecting and storing spent solvent in a first vessel for a period of time sufficient to permit the spent solvent to separate into an upper aqueous phase and a lower oil phase;
2. discharging the separated, stored spend solvent from the first vessel by sequentially discharging the oil phase and the aqueous phase through an automatic liquid phase detector-transmitter which includes an in-line electrical conductometric probe having two electrodes exposed to the stream of the two phases and which generates an appropriate electrical signal indicating the presence or absence of the aqueous phase or the oil phase as either phase passes through the detector-transmitter; and
3. conducting the oil phase from the first vessel through conduit means to a seond vessel and the aqueous phase from the first vessel through conduit means to waste by means of appropriate valves which are controlled by a programming means which is actuated by the elctrical signal generated by the detector-transmitter, said process further comprising automatically regenerating the reclaimed oil phase by adding an amount of water to said second vessel equal to the amount of aqueous phase discharged to waste and an amount of fresh oil to said first vessel equal to the amount of oil phase lost during the cleaning operation, said automatic regeneration being controlled by said programming means.

3. The process of claim 2 wherein the oil is a chlorocarbon.

4. The process of claim 2 wherein the oil is a chlorofluorocarbon.

5. The process of claim 4 wherein the chlorofluorocarbon is 1,1,2-trichloro-1,2,2-trifluoroethane.

* * * * *